United States Patent
Leach et al.

(10) Patent No.: US 9,604,159 B2
(45) Date of Patent: *Mar. 28, 2017

(54) LIQUID SEPARATION FROM ADIPOSE TISSUE

(71) Applicant: Biomet Biologics, LLC, Warsaw, IN (US)

(72) Inventors: Michael D. Leach, Warsaw, IN (US); Jason Chavarria, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 326 days.

This patent is subject to a terminal disclaimer.

(21) Appl. No.: 14/033,944

(22) Filed: Sep. 23, 2013

(65) Prior Publication Data

US 2014/0021147 A1     Jan. 23, 2014

Related U.S. Application Data (60) Division of application No. 12/758,119, filed on Apr. 12, 2010, now Pat. No. 8,540,078, which is a
(Continued)

(51) Int. Cl.
*B01D 21/26*     (2006.01)
*B04B 5/04*     (2006.01)
(Continued)

(52) U.S. Cl.
CPC ....... *B01D 21/262* (2013.01); *B01D 17/0217* (2013.01); *B04B 3/00* (2013.01);
(Continued)

(58) Field of Classification Search
CPC .............. B01D 17/0217; B01D 21/262; A61B 2017/00969; A61M 1/0066; A61M 1/0068;
(Continued)

(56) References Cited

U.S. PATENT DOCUMENTS 148,513 A     3/1874    Senderling
925,856 A     6/1909    Wilder
(Continued)

FOREIGN PATENT DOCUMENTS

WO    WO-2010148008 A1    12/2010
WO    WO2010148008 A1    12/2010

OTHER PUBLICATIONS

"Genesis Biosystems, Innovations in Regeneration, LipiVage® Fat Harvest, Wash & Transfer Systems," http://www.genesisbiosystems.com/product/lipivage-systems.html, 8 sheets, (2009).
"Tissu-Trans® Filtron Systems; 500 to 2000cc Fat Harvest Filter Systems"; Shippert Medical Technologies Inc., www.shippertmedical.com, 2 sheets, No Date.
International Preliminary Report on Patentability and Written Opinion mailed Dec. 29, 2011 for PCT/US2010/038701 claiming benefit of U.S. Appl. No. 12/485,619, filed Jun. 16, 2009.
(Continued)

*Primary Examiner* — David C Mellon
(74) *Attorney, Agent, or Firm* — Schwegman Lundberg & Woessner, P.A.

(57) ABSTRACT

Extracting or removing at least a portion of liquid phase from a whole sample using a centrifugal force is disclosed. Centrifugal forces are used to apply pressure to a whole sample and drive a liquid phase through a passage region that can be perforated and/or porous and maintain a drier portion within a separation container. The whole sample can be dried, which includes a remaining sample where excess or a selected amount of liquid is removed. Direct access to the separation container or area can then be made to provide for an efficient withdrawal of the drier material from the separation container.

22 Claims, 10 Drawing Sheets

Related U.S. Application Data continuation-in-part of application No. 12/485,619, filed on Jun. 16, 2009, now Pat. No. 8,790,519.

(51) Int. Cl.
  *B04B 11/06* (2006.01)
  *A61B 17/00* (2006.01)
  *B01D 17/02* (2006.01)
  *B04B 3/00* (2006.01)

(52) U.S. Cl.
  CPC ............ *B04B 5/0442* (2013.01); *B04B 11/06* (2013.01); *A61B 2017/00969* (2013.01); *A61M 2202/08* (2013.01)

(58) Field of Classification Search
  CPC .... A61M 2202/08; B04B 3/00; B04B 5/0442; B04B 7/08; B04B 7/12; B04B 7/16; B04B 7/18; B04B 9/02; B04B 9/04; B04B 11/06; B04B 15/12
  See application file for complete search history.

(56) References Cited

U.S. PATENT DOCUMENTS

| | | | |
|---|---|---|---|
| 3,199,775 A | 8/1965 | Drucker | |
| 3,443,695 A | 5/1969 | O'Neill | |
| 3,463,316 A | 8/1969 | Fierstine | |
| 3,567,030 A | 3/1971 | Loeffler et al. | |
| 3,864,256 A | 2/1975 | Hultsch et al. | |
| 3,882,716 A | 5/1975 | Beiman | |
| 4,109,853 A | 8/1978 | Ruegg | |
| 4,118,248 A | 10/1978 | Lacher | |
| 4,244,916 A | 1/1981 | Guigan | |
| 4,302,332 A | 11/1981 | Hayakawa et al. | |
| 5,409,833 A | 4/1995 | Hu et al. | |
| 5,788,662 A | 8/1998 | Antanavich et al. | |
| 7,294,269 B2 | 11/2007 | Kim et al. | |
| 7,708,152 B2 | 5/2010 | Dorian et al. | |
| 7,824,559 B2 | 11/2010 | Dorian et al. | |
| 7,866,485 B2 | 1/2011 | Dorian et al. | |
| 8,540,078 B2 | 9/2013 | Leach et al. | |
| 8,790,519 B2 | 7/2014 | Leach et al. | |
| 2004/0029696 A1 | 2/2004 | Mackel et al. | |
| 2005/0025755 A1 | 2/2005 | Hedrick et al. | |
| 2005/0123895 A1 | 6/2005 | Freund | |
| 2005/0161392 A1 | 7/2005 | Duby | |
| 2006/0175242 A1 | 8/2006 | Dorian et al. | |
| 2006/0175244 A1 | 8/2006 | Dorian et al. | |
| 2006/0175424 A1 | 8/2006 | Tatum et al. | |
| 2006/0213374 A1 | 9/2006 | Shippert | |
| 2009/0289014 A1 | 11/2009 | Hoeppner | |
| 2010/0226909 A1 | 9/2010 | Hecker et al. | |
| 2010/0314334 A1 | 12/2010 | Leach et al. | |
| 2010/0317099 A1 | 12/2010 | Leach et al. | |

OTHER PUBLICATIONS

International Search Report and Written Opinion mailed Nov. 18, 2010 for PCT/US2010/038701 claiming benefit of U.S. Appl. No. 12/485,619, filed Jun. 16, 2009.

John A. Millard MD., "Revolutionizing Autologous Fat Transfer/Fat Grafting: Vaser® Lipo System and Shipper Tissu-Trans®", Apr. 2009, 4 sheets.

Ron D. Shippert MD, "Original Scientific Presentation, Vacuum Pressures During Autologous Fat Transfer (AFT): A Study of the Closed Syringe Type and Other Aspirator Pressures", vol. 26, Dec. 28, 2008, pp. 230-235.

Second Office Action for China Patent Application No. 2010800272078 dated Oct. 11, 2014.

LIQUID SEPARATION FROM ADIPOSE TISSUE

CROSS-REFERENCE TO RELATED APPLICATIONS

This application is a divisional of U.S. patent application Ser. No. 12/758,119 filed on Apr. 12, 2010, which issued as U.S. Pat. No. 8,540,078 on Sep. 24, 2013; which is a continuation-in-part of U.S. patent application Ser. No. 12/485,619 filed on Jun. 16, 2009, which issued as U.S. Pat. No. 8,790,519 on Jul. 29, 2014. The entire disclosures of the above applications are incorporated herein by reference.

FIELD

The present disclosure is directed to liquid separation from a wet material, and particularly to liquid separation from adipose tissue.

BACKGROUND

This section provides background information related to the present disclosure which is not necessarily prior art.

In an anatomy, such as a human anatomy, adipose tissue can store energy for future use. Adipose tissue can be stored at various locations on the human anatomy. At some locations whole adipose tissue can be accessed and removed. For example, during a liposuction procedure, adipose tissue can be suctioned or aspirated from subcutaneous regions.

One procedure to dry whole adipose tissue includes using normal gravity separation through a filter to separate the liquid phase or a liquid from the whole adipose tissue.

SUMMARY

This section provides a general summary of the disclosure, and is not a comprehensive disclosure of its full scope or all of its features.

Whole adipose tissue can be withdrawn from a patient using various techniques, such as aspiration or resection. Adipose tissue suction, also referred to as liposuction, can remove a sample of whole adipose tissue. The whole adipose tissue sample can include all phases or portions of the adipose tissue of a patient. For example, the adipose tissue can include adipocytes, liquid or proteins between adipocytes, or other portions. Removal of a liquid from the adipose tissue can result in firmer and denser adipose particles. The firmer or denser adipose tissue particles can be used in various procedures, such as cosmetic procedures, for maintaining a contour or shape of a reconstruction of a patient.

Removal of at least a portion of a liquid from adipose tissue is enhanced with a system that can forcibly remove the liquid phase from the adipose tissue. As disused further herein, adipose tissue can be placed in a single container and a force applied to the adipose tissue to force the liquid phase from the adipose tissue. For example, centrifugal forces can be used to direct a liquid out from an adipose tissue sample into a liquid separation container or sequestering area.

According to various embodiments, a method of removing a liquid phase from a whole adipose tissue sample is disclosed. The method can include obtaining a whole adipose tissue sample from a patient, placing the obtained whole adipose tissue sample into a first separation region of a separation container, and surrounding the separation container with an exterior container. Then spinning the separation container within the exterior container about a central axis of the separation container can be done to place a centrifugal force on the obtained whole adipose tissue sample placed in the separation container. The method can also include moving a volume of a liquid phase through a passage portion of the separation container while spinning the separation container and containing adipose particles of the whole adipose tissue sample within the first separation region. The method can then contain the volume of the liquid phase in a second separation region of the separation container and allow collecting adipose particles in a withdrawal area of the first separation region after the volume of the liquid phase has been removed and withdrawing the adipose particles while maintaining the separation container within the exterior container.

According to various embodiments, a method of removing a liquid phase from a whole adipose tissue sample is disclosed. The method can include collecting a whole adipose tissue sample, moving the collected whole adipose tissue sample into an adipose particle region of a separation container. The method also includes spinning the separation container to move at least a portion of the whole adipose tissue sample adjacent to a passage portion of the separation container and forcing at least a portion of a liquid phase of the whole adipose tissue to move through the passage portion. The method can also include collecting the portion of the liquid phase forced through the passage portion in a liquid collection region of the separation container and withdrawing the adipose particles from the adipose particle region through a withdrawal tube.

According to various embodiments, a method of removing a liquid phase from a whole adipose tissue sample is disclosed. The method includes positioning a whole adipose tissue sample in an adipose particle collection region of a separation container, applying a centrifugal force to the whole adipose tissue sample to force a selected volume of a liquid phase of the whole adipose tissue sample through a passage portion. The method further includes sequestering the selected volume of the liquid phase in a liquid collection region and removing the application of the centrifugal force after the selected volume of the liquid phase is sequestered. The method can also include collecting the remaining adipose tissue sample in a sump of the adipose particle collection region and withdrawing the collected remaining adipose tissue sample from the sump.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
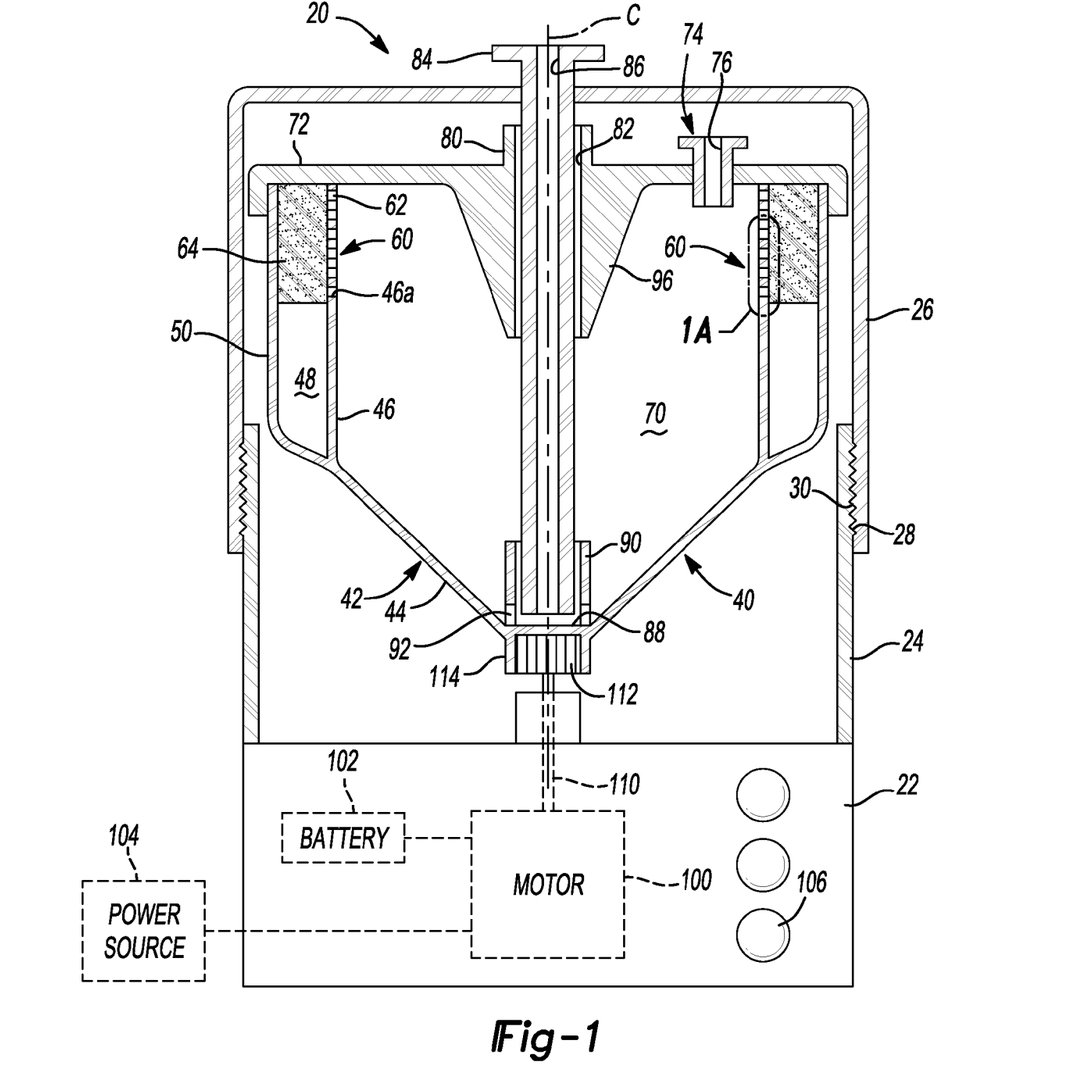
FIG. 1 illustrates a cross-section view of a separation system.

With reference to FIG. 1, a liquid removal system 20 is illustrated. The liquid removal system 20 can include a base 22 from which an exterior or outer wall 24 extends. The base can be the base or motor containing portion used with the Vortech® concentration system sold by Biomet Biologics, Inc. of Warsaw, Ind., USA. The outer wall 24 can interconnect with an exterior lid 26 via an interconnection, such as a threaded interconnection with wall threads 28 and a lid thread 30. The outer wall 24 and the outer lid 26 form an exterior container that can surround a region in which a separation container 40 is positioned.

The separation container 40 can include an exterior wall 42 that has a lower angled portion 44, which can be angled at about 60 degrees to about 80 degrees, such as about 75 degrees relative to a central axis C. An upper interior wall 46 can be angled less than the lower angled wall 44 or substantially parallel to the central axis C of the liquid removal system 20. According to one example, the upper wall can be angled at about one (1) degree to about five (5) degrees, such as about one degree to about three degrees, relative to the central axis C. The separation container 40 can further include an annular collection basin 48 formed by the inner wall 46 and an exterior basin wall 50. The exterior basin wall can be substantially parallel to the central axis C. The annular collection basin 48 can be a liquid separation area or a liquid sequestering region.

The separation container 40 can be substantially symmetrical around the central axis C, such as an annular container. It will be understood, however, that the separation container 40 can also include other appropriate configurations such as hexagonal, octagonal, or other symmetrical configurations. It will be further understood, that the separation container 40 need not be symmetrical around the central axis C.

The inner wall 46 can include passage portion or section. The passage portion or section can include a perforated or screen portion 60 near an upper end 62 of the inner wall 46 and/or a foam and/or felt member 64. The passage portion can allow at least a selected volume or material to pass to the basin 48. The passage portion can have selected features, as discussed herein, for selectively removing material from a whole material.

The perforated portion 60 can extend substantially around the central axis C in the inner wall 46 of the separation container 40. Positioned on an exterior of the inner wall 46 can be a filter 64. The filter 64 can fill the area between the perforated region 60 and the basin 48. Accordingly, the filter 64 can be positioned such that any material that passes through the perforated portion 60 into the basin 48 must pass through the filter material 64.

The filter material 64 can include foam or felt material that includes passages or pores. The pores or passages can be formed or include an appropriate diameter or defined as a felt weight. For example, the filter material can be a felt that weighs about 22 ounces (oz) per square yard (22 oz felt). The felt, however, may include a weight of 10 oz to about 30 oz felt. The filter material can be polyester felt including the 22 oz. felt sold by Superior Felt & Filtration, LLC. having a place of business at Ingleside, Ill.

Figure 1A:
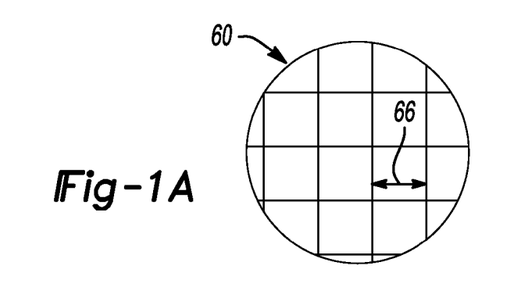
FIG. 1A illustrates a detail view of a passage region of the separation system.
Figure 1B:
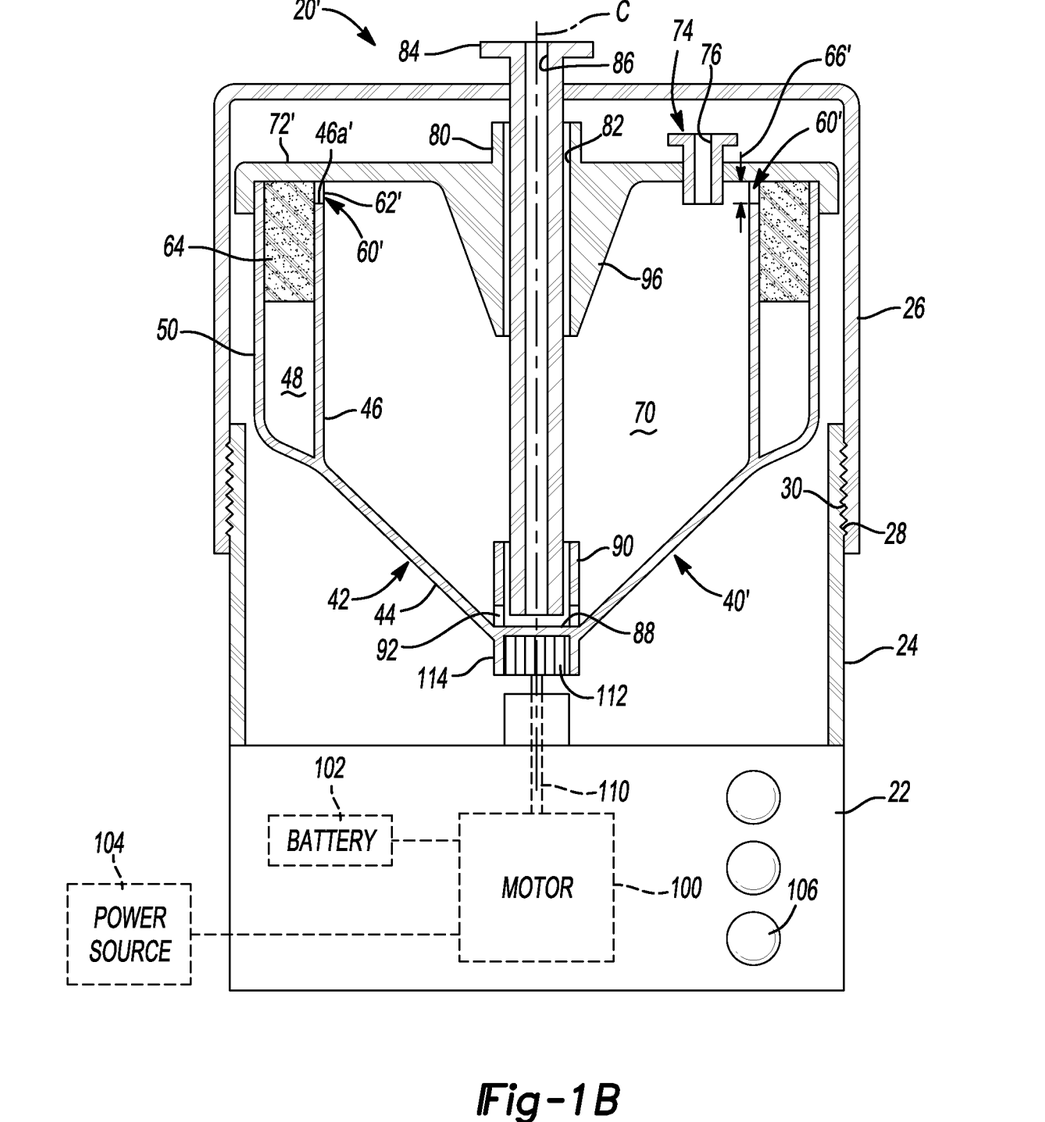
FIG. 1B illustrates a perspective view of a separation container according to various embodiments.
Figure 2:
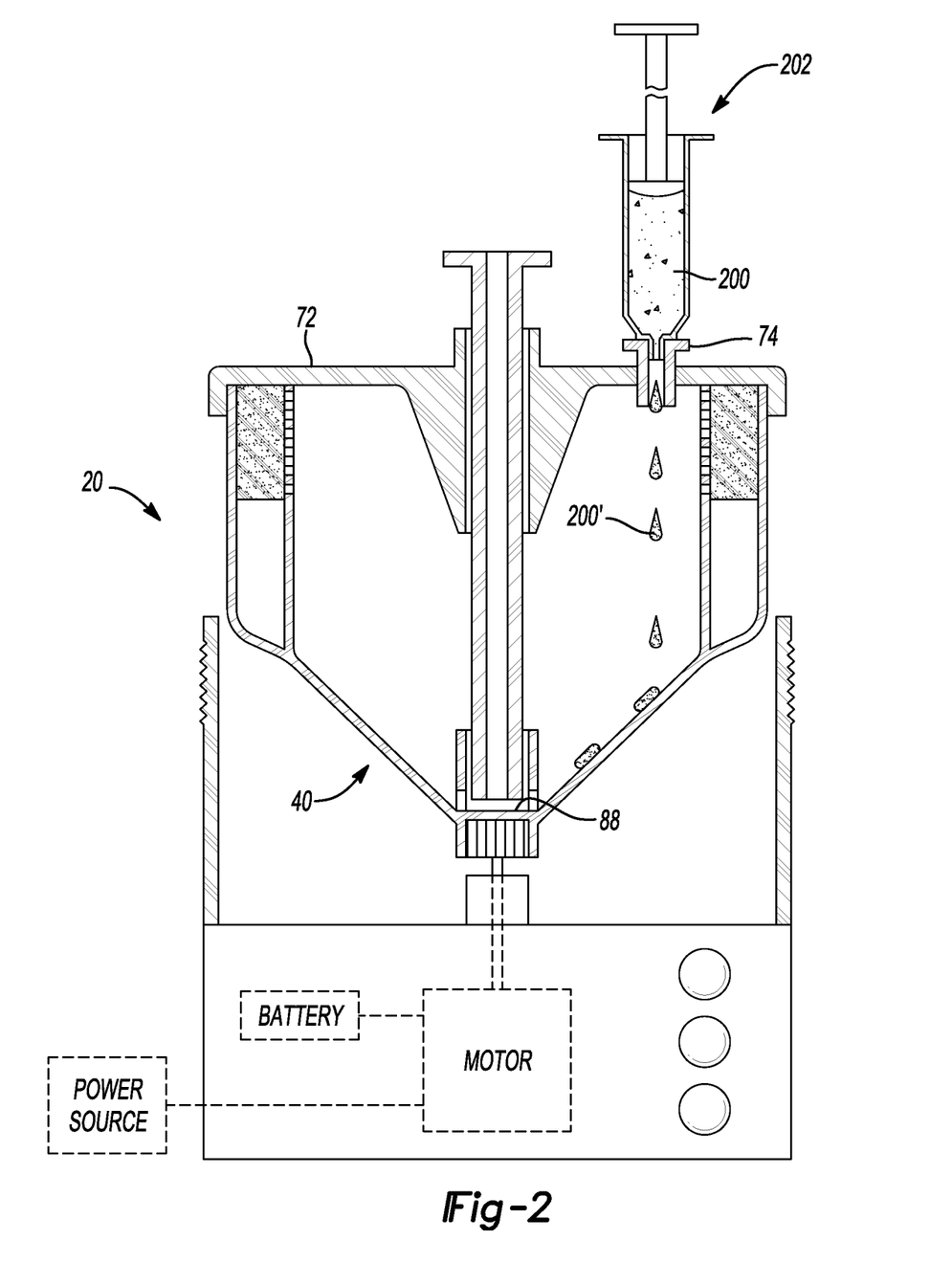
FIGS. 2-5 illustrates a method of separating liquid from adipose tissue.

Also the perforated region 60 can include a passage or perforation that is any appropriate dimension 66, such as about 0.05 inches, as illustrated in FIG. 1A. According to various embodiments, the perforated region 60 can include a gap or perforated region 60', illustrated in FIG. 1B. The wall 46" need not be perforated over a distance of the wall, but rather the lid 72 can be spaced a perforated distance 66' from a top 46a' of the wall 46'. The filter material 64 can be positioned in the basin region 48 exterior to the interior separation region 70 and the liquid, as discussed herein, can enter the basin through the perforated distance 66'. The remainder portions of the separation system 20' are like those discussed herein, and not discussed in further detail here.

As discussed further herein, the dimension 66 of the perforated region 60 or the porous size or filter size of the filter material 64 can be selected to maintain a material within a central separation or collection area 70, also referred to as an adipose particle separation region, of the separation container 40 while allowing only a selected material to enter the basin region 48.

It will be further understood that the filter 64 and the perforated region 60 need not be used together, and only one may be selected. Accordingly, the filter 64 could fill the entire region above a first terminal portion 46a of the inner wall 46 or the perforated region 60 could be provided with an appropriate pore dimension 66 to achieve a selected separation result. Generally, as discussed herein, the pore dimension 66 or pore size of the filter 64 is selected to allow substantially only liquid of a whole adipose tissue sample to pass to the basin 48.

The separation container 40 can be closed or contained with an inner lid 72. The inner lid 72 can be fit over the exterior wall 50. The inner lid 72 can seal the separation container 40 including from the region contained within the outer lid 26 and outer wall 24. The lid 72 can include a passage for a first portal 74 that can include a cannula 76. The cannula 76 can allow for filling the separation area 70 from the exterior of the separation container 40. The first portal 74 can include a luer lock or fitting to allow for interconnection of a syringe or other member to deliver a material to the separation area 70 of the separation container 40.

The inner lid 72 can also form a second portal 80 which includes a second cannula 82 through which an elongated member or tube 84 having a withdrawal cannula 86 can be passed. The withdrawal member 84 can be fixed or connected with the exterior lid 26 or be provided separate therefrom. The elongated member 84 can also or alternatively be fixed to the separation container. The withdrawal member 84, however, can extend towards or to an interior or sump region 88 of the separation container.

Near the sump region 88 can be a stabilization wall or structure 90 that has a passage or bore 92 that can allow material to reach the sump region 88 of the separation container 40. The elongated member 84 can be connected or formed with the wall 90. Material can then be withdrawn through the withdrawal cannula 86 through the external or outer lid 26 without dismantling the outer lid 26 from the outer wall 24. The lid 72 can also define a stabilization portion 96 that assists in stabilizing the withdrawal member 84 during a separation operation of the separation container 40, as discussed further herein. Briefly, the entire separation container and the inner lid 72 can be rotated around the central axis C to force or assist in moving a material through the perforated region 60 and the filter 64.

According to various embodiments, the separation container 40 illustrated in FIG. 1 can be connected with the base 22 that can house a motor 100 that can be powered with an appropriate power source such as a battery 102 that can provide a DC current or a power source 104 that can provide an alternating current or a direct current. Additionally, the power source or battery can be internal or external to the base 22. Various control knobs or buttons 106 can also be provided on the base to control the motor 100. The motor 100 can be controlled for speed, duration, or other appropriate periods.

The motor 100 can be connected to an axle 110 that extends from the base 22 to a gear or connecting member 112. The connecting member 112 can be fixedly connected to the axle 110 and can be removeably or selectively connected to a receiving portion 114 of the separation container 40. The receiving portion 114 can connect with the gear 112 which can be driven by the axle 110 from the motor 100 to rotate the separation container 40. The separation container can be rotated around the central axis C to induce a centrifugal force within the separation container 40 to move a material against the wall 46 and the perforated region 60 and/or the filter 64. As discussed further herein, the centrifugal force can be used to separate a material placed in the separation container 40.

The separation container 40 can be spun or rotated at various speeds for variable times to cause a separation of a material or a phase of the material placed within the separation container 40. For example, separation container can be spun at about 1000 rotations per minute (rpms) for about one minute, then 2000 rpms for three minutes and then slowed gradually to a stop. As a further example, the whole adipose sample can be spun in the separation container 40 at about 2000 rpms for about 30 seconds. Other examples can allow the separation container to be spun at a single selected speed (not counting for ramp up and ramp down speeds) at about 1000 rpms to about 5000 rpms for 10 seconds to about 5 minutes. Another exemplary separation scenario can include spinning that separation container 40 with the sample therein at a speed of about 100 rpms to about 4000 rpms for a time of about five seconds to about 30 seconds. This can include a spin scenario at about 2500 to about 3500 rpms for about five seconds to about ten seconds. It will be understood, however, that any other appropriate separation spin rate or run time can be used.

According to various embodiments, the liquid removal system 20 illustrated in FIG. 1 can be used to separate a liquid phase or material from a whole adipose tissue sample. The whole adipose tissue sample can be withdrawn directly from a patient, such as with aspiration during liposuction or similar procedures. Alternatively, or in addition thereto, whole adipose samples can be excised from a patient during an operative procedure, such as a cosmetic or orthopedic procedure.

With reference to FIGS. 2-5, the liquid removal system 20 can be used to separate a liquid phase from a whole adipose tissue sample such that the non-liquid phase or adipose particles are maintained alone near or at the sump 88 of the separation container 40. Initially, a whole adipose sample 200 can be introduced into the separation container 40 via the filling port 74. The whole adipose tissue sample 200 can be contained or delivered from within a syringe assembly 202 and expressed into the separation container 40 as a stream or droplets 200'. The whole adipose tissue sample 200 can also be positioned directly into the separation container by removal of the inner lid 72. However, the filling port 74 can allow for maintaining the separation container 40 in a substantially sterile environment by not requiring the lid 72 to be removed while introducing the whole adipose tissue sample 200. Accordingly, within the cannula 76 can be a one way valve or sterile foam to assist in maintaining the sterility and cleanliness of the separation container 40. It will also be understood that any appropriate device can be used to connect with the filling port 74. For example, a hose or other member can interconnect a collection beaker with the separation container 40 for introducing the whole adipose tissue sample 200 into the separation container 40.

Figure 3:
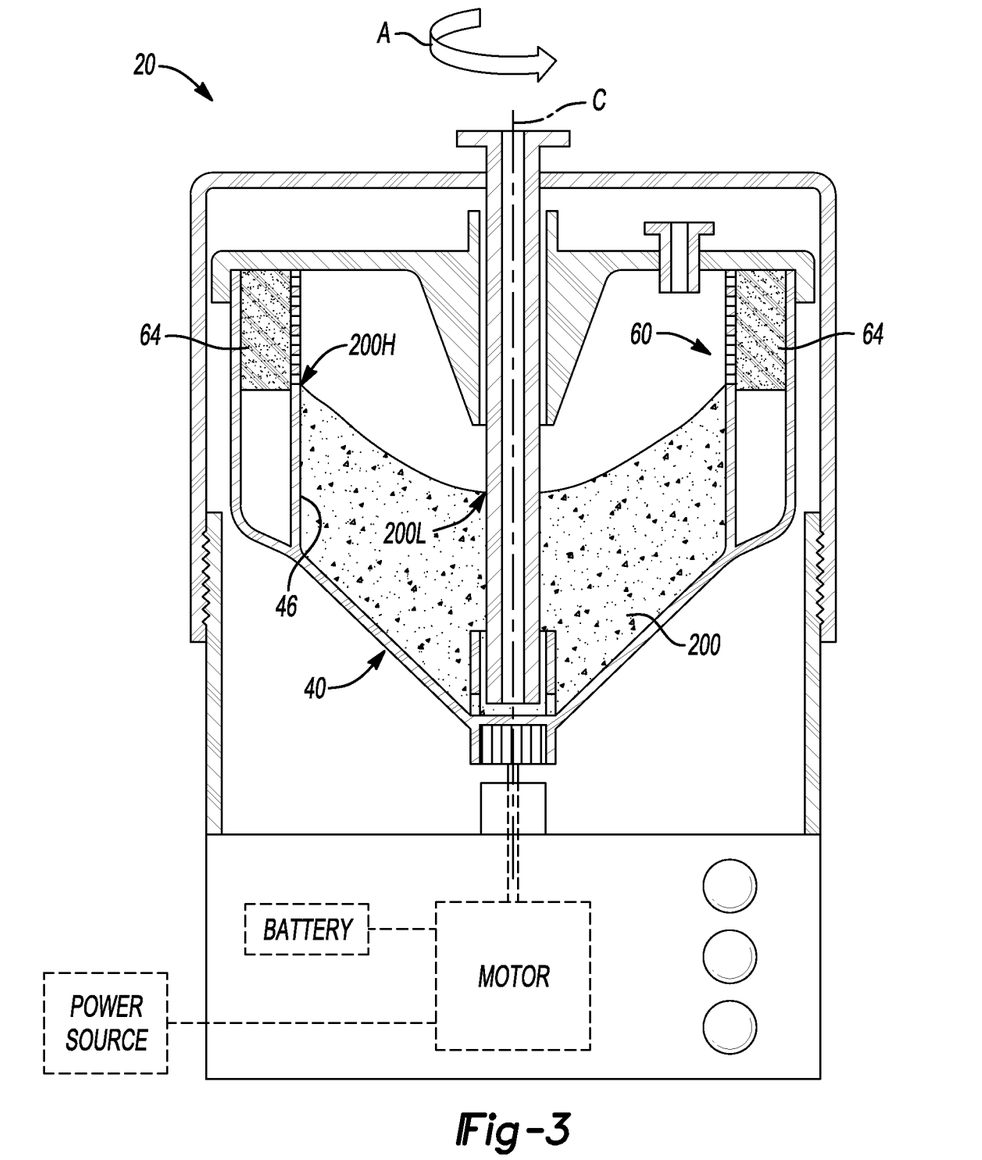

With reference to FIG. 3, once an appropriate amount of whole adipose sample 200 is placed in the separation container 40, the separation cycle can begin. As discussed above, the separation container 40 can rotate around the central axis C. For example, the separation container 40 can rotate in a substantially counter clockwise direction indicated by arrow A in FIG. 3. The separation container 40, upon beginning rotation around the central axis C, can induce a centrifugal force on the whole adipose sample 200. With the introduction of the centrifugal forces, the whole adipose tissue sample 200 can begin being pressed or moved against the wall 46 of the container 40. This can cause a high region 200*h* of the whole adipose tissue sample away from the central axis C and a low region 200*l* near the central axis C. As the whole adipose tissue sample 200 continues to rise and the centrifugal force is increased, soon a portion of the whole adipose tissue sample will become near or adjacent to the channel or perforated region 60 and the filter 64.

Figure 4:
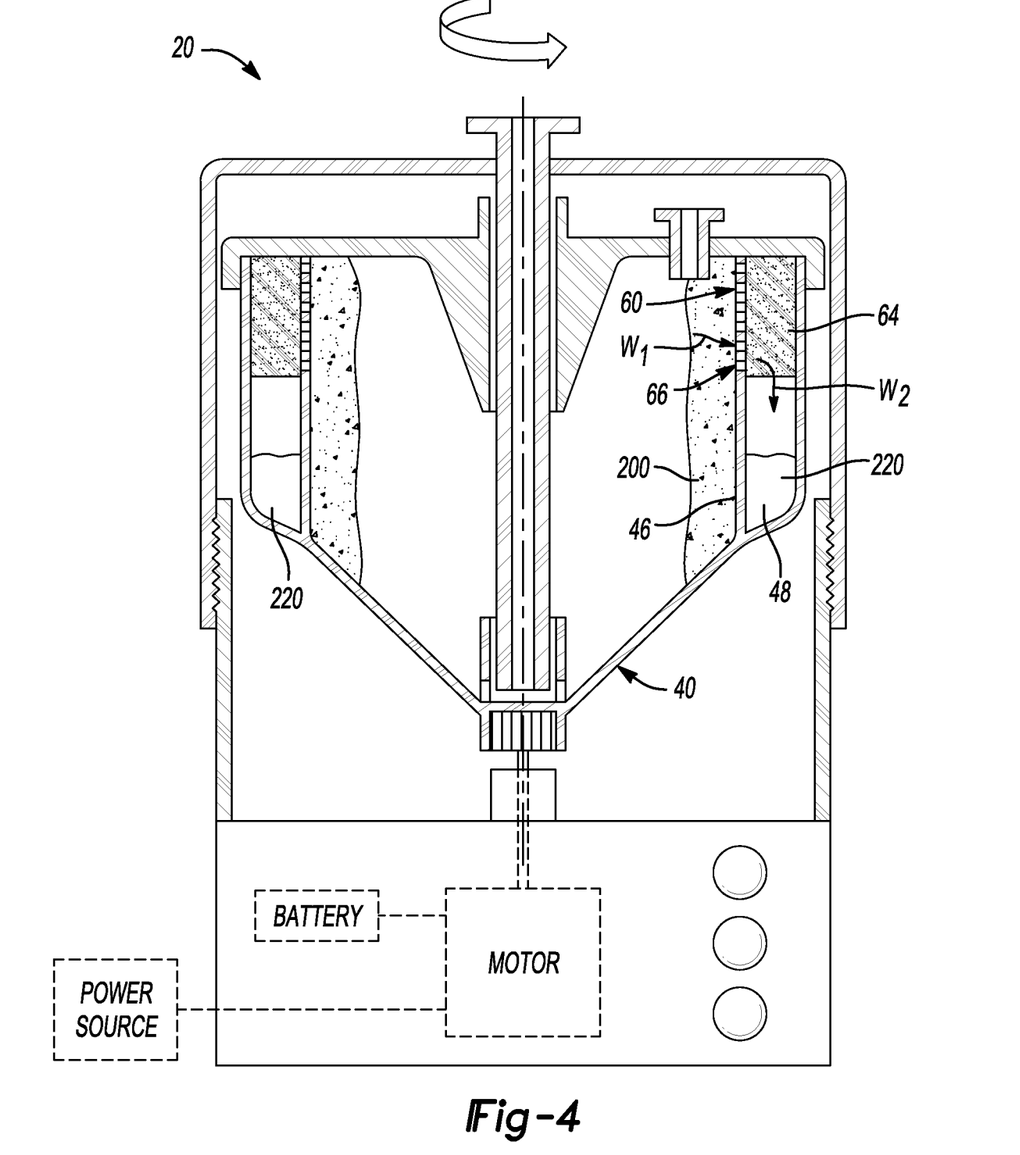

With reference to FIG. 4, at a selected rotational speed of about 100 to about 5000 rpms, including about 2000 rpms to about 3000 rpms, and further exemplarily including about 3200 rpms, to induce an appropriate and selected force on the whole adipose tissue sample 200, the whole adipose tissue sample 200 can be substantially pressed against the wall 46 of the separation container 40. When pressed against the wall 46, near the perforated region 60, a portion of the whole adipose tissue sample 200 that includes a size smaller than the passage diameter 66 of the perforated region 60 and/or the filter 64 can move through the perforated region 60 in the direction of arrow w1. The liquid or water phase of the whole adipose tissue sample 200 can be allowed to move through the perforated region 60. That is, the pore diameter 66 of the perforated region 60 can be provided such that a water (e.g. aqueous) or liquid phase 220 is allowed to move through the perforated region 60 while maintaining a fat or adipose particle phase or portion 230 of the whole adipose tissue sample 200 within the separation region 70 of the separation container 40.

The liquid or water phase 220 can further move through the perforated region 60 into the basin 48 by moving generally in the direction of arrow w2 either during or after spinning of the container 40. The liquid 220 can be collected in the basin 48 by action of the centrifugal force on the whole adipose tissue sample 200 placed within the separation container 40.

The separation container 40 can be spun at a selected rate for a selected time to achieve an appropriate separation of the liquid phase 220 from the whole adipose tissue sample 200. For example, it can be selected to remove an appropriate percentage, such as 30%, 50%, 70%, 80%, or 90% of the liquid from the whole adipose tissue sample 200. This can produce an adipose particle 230 that has less liquid than the whole adipose tissue sample 200. It will be further understood, however, that only a minimal amount of the liquid phase 220 may be selected to be removed from the whole adipose tissue sample 200.

Also, the volume of the basin 48 relative to the volume of the whole adipose tissue sample 200 placed in the separation region 70 can determine the amount of liquid removed. For example, the separation region 70 can hold 180 mL of the whole adipose tissue sample 200 and the basin 48 can hold 90 mL. Thus, the liquid phase 220 removed would be about 50% of the whole adipose tissue sample 200. As will be understood, however, providing or designing different ratios of the volumes of the two regions (e.g. separation region 70 and the basin 48) can form different separation percentages. For example, the separation region 70 of about 180 mL and the basin 48 can be about 20 mL and this would about 20% removal of the whole adipose tissue sample 200. As otherwise stated, the amount of the liquid phase 220 removed can be limited or determined by the volume of the basin 48.

Also, rather than providing or including different volume differences, or in addition thereto, the amount of liquid 220 removed, as a percentage or ratio of the whole adipose tissue sample 200, can be altered by changing the volume of the whole adipose tissue 200 initially introduced. For example, a volume of 150 mL of the whole adipose tissue sample 200 can be introduced into the separation region 70 and the about 90 mL of the basin 48 can be filled with the liquid phase 230. Thus, the percentage of the adipose particles 230 retained from the initial whole adipose tissue sample 200 can be about 40%. Accordingly, the density or ratio of the retained or remaining adipose tissue sample 230 can be selected based on the initial volume placed in the separation region 70 while having a volume of the basin region 48 fixed.

Generally, it is selected to have the density of the remaining adipose particles 230 firm enough for selected procedures, such as cosmetic procedures, but fluid enough to pass though an implantation syringe. Denser adipose tissue samples can be maintained in a selected area of an anatomy in a selected contour or shape for longer periods due to the absence of the liquid phase, which can dissipate quickly in the anatomy. Thus, the drier adipose particles 230, compared to the whole adipose tissue sample 200, can maintain a selected contour or shape in the anatomy longer than a whole adipose tissue sample 200.

Regardless, the pore diameter 66 of the perforated region 60 can be provided to allow only the liquid phase to pass through. Similarly, or in addition to the perforated region 60, the filter 64 can be provided to assist in the liquid phase removal from the whole adipose tissue sample 200. For example, the filter 64 can be alone placed at an upper or top region of the separation container 40 between the inner separation region 70 and the outer basin 48. The filter 64 can include an appropriate pore size, again, so that only the liquid phase is removed from the whole adipose tissue sample 200.

Figure 5:
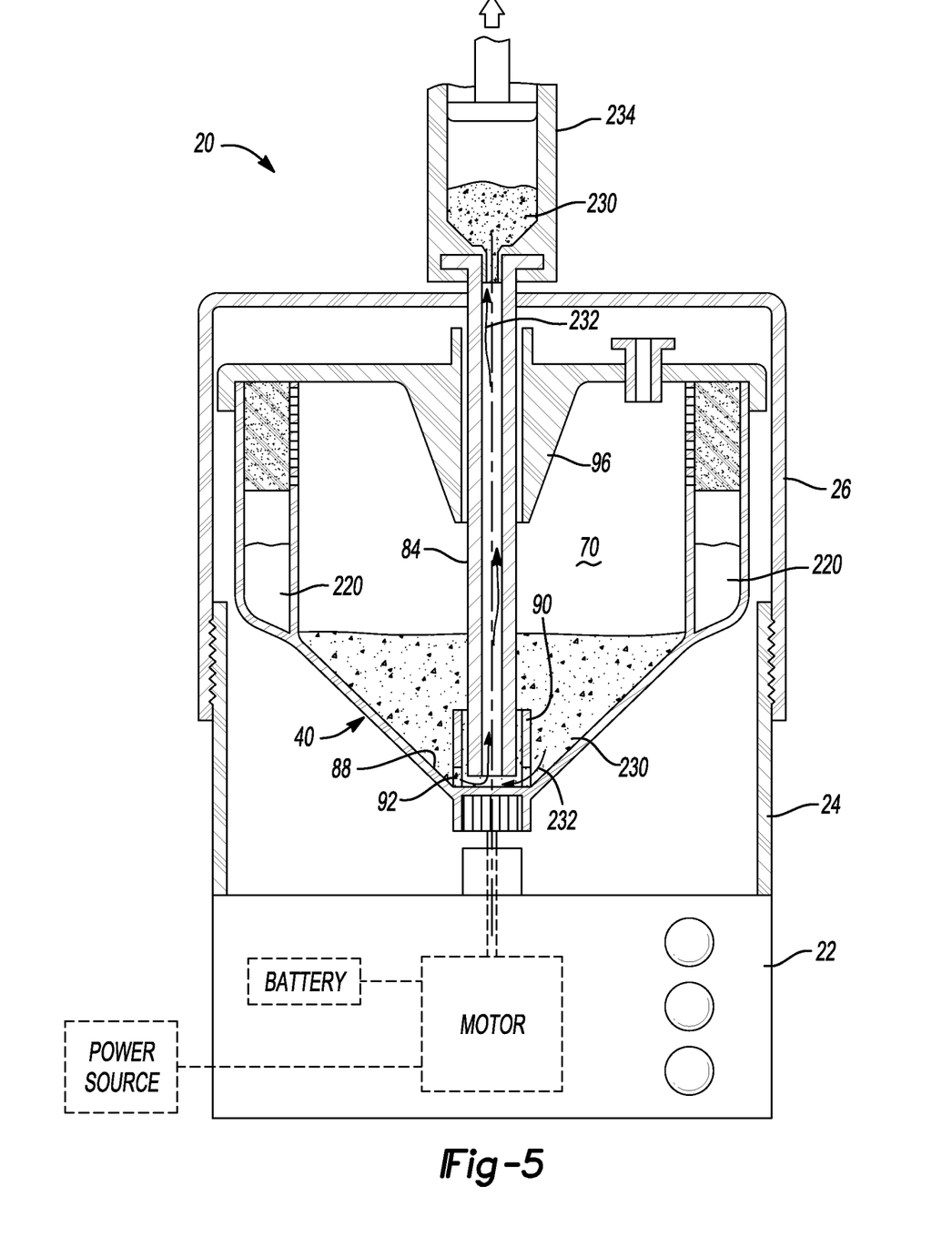

After appropriate period of spinning, the separation container 40 can be halted. With reference to FIG. 5, after the removal of the liquid phase 220 has been completed, the separation container 40 can be halted and the remaining sample, which can be a substantially adipose particle portion 230 of the whole adipose tissue sample 200 can be contained within the inner separation container or adipose particle area 70. The adipose particle portion 230 can be a portion of the whole adipose sample 200 with excess or a selected amount of liquid removed from the whole adipose sample 200. It is understood that the adipose particle portion 230 can be drier than the whole adipose sample 200 while still including a selected volume or concentration of liquid from the whole adipose tissue sample 200.

The adipose particle portion 230 can then be withdrawn through the ports or passages 92 near the sump 88 generally in the direction of arrow 232. The adipose particles 230 can be withdrawn through the withdrawal member 84 into an adipose particle syringe 234. The adipose particle portion 230 can be withdrawn into the syringe 234 through any appropriate mechanism, such as forming a low pressure region within the syringe 234. Accordingly, the adipose particles 230 can also be withdrawn through the withdrawal cannula or member 84 with any appropriate mechanism, such as connecting a tube and forming a vacuum to withdraw the adipose particles 230 from the separation container 40.

The passages 92 can allow the adipose particles 230 to be withdrawn from the separation container 40 through the withdrawal member 84. It will be understood, however, the stabilization wall 90 is not required and the withdrawal cannula 80 could be positioned near or at the sump 88. Further, although a sump 88 can increase efficient withdrawal and high volume collection of the adipose particles 230, it will be understood that the sump 88 is not required and the separation container 40 could include a substantially flat or planar bottom.

The separation container 40, therefore, can be maintained in its position relative to the base 22 during withdrawal of the adipose particles 230 from the separation container 40. Similarly, the outer lid 26 can be maintained connected with the outer wall 24 during withdrawal of the adipose particles 230 from the separation container 40. The withdrawal port or member 84 can be maintained within the separation container 40 during the separation and withdrawal to allow for efficient one step separation and withdrawal of the drier (e.g. with excess or a selected amount of liquid separated or removed) adipose particles 230.

The withdrawal cannula or member 84 can be interconnected with the external lid 26, either before or after positioning the lid 26 over the separation container 40. The withdrawal cannula or member 84 can be fixed relative to the separation container 40 as the separation container 40 rotates around the central axis C. Alternatively, the withdrawal port or member 84 can be fixed to the separation container 40, either at the stabilization wall 90 or the lid stabilization portion 96 and rotate with the separation container 40 and substantially freely of the outer lid 26. Regardless, the withdrawal port or member 84 can be maintained within the separation container 40 during substantially all portions of the separation procedure of the whole adipose sample 200 for efficient removal of the adipose particles 230 once the liquid phase 220 has been removed from the whole adipose sample 200.

Figure 6:
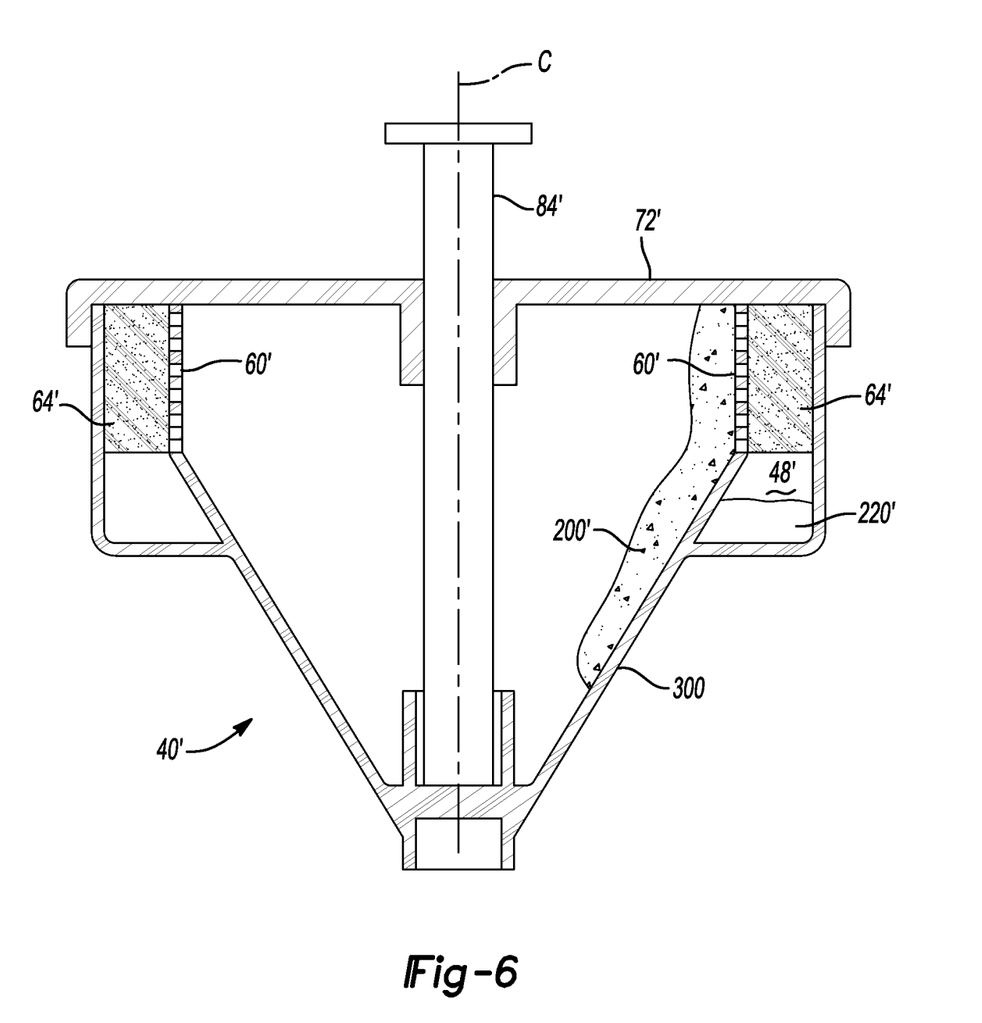
FIG. 6 illustrates a cross-section view of a separation container according to various embodiments.

With reference to FIG. 6, according to various embodiments, a separation container 40" is illustrated. The separation container 40" can include portions that are similar to the separation container 40 illustrated above. The similar portions are those portions illustrated with the same reference numeral augmented with a double prime and will not be described in detail herein. The separation container 40", however, can include an augmented or different geometry from the separation container 40. For example, the separation container 40" can include substantially completely conical internal wall 300 extending to the perforated region 60" which can also be substantially conical or parallel to a central axis C.

The substantially completely conical wall 300 can allow the whole adipose tissue sample 200 to be directed substantially completely and quickly to the perforated region 60″. The liquid phase 220 can still be collected and maintained within external collection region 48″ that can be designed to cooperate with the substantially conical wall 300 of the separation container 40″ of the liquid removal system 20.

Excess or a selected amount of a liquid phase 220 from the whole adipose tissue sample 200 can then be removed. The adipose particles 230 need not be completely dry or absent of all liquid, but may only be made drier by removing a selected amount of the liquid phase or water 220, such as removing about 40% to about 60%, such as about 50% from the whole adipose tissue sample 200, as discussed above. The drier adipose particles 230 can then be withdrawn from the separation container 40″, as discussed above.

Figure 7:
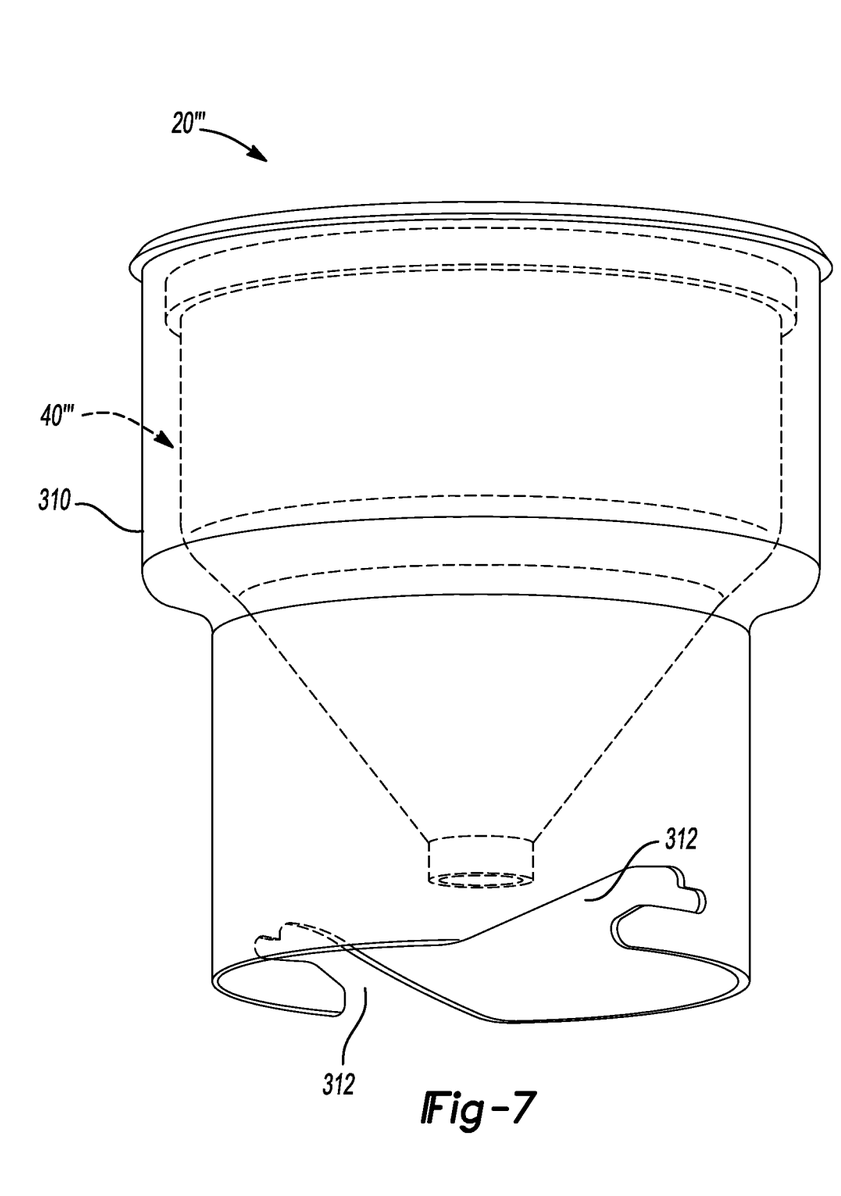
FIG. 7 illustrates a perspective view of a separation container according to various embodiments.

According to various embodiments, FIG. 7 illustrates a separation system 20′″ (without a motor base). The separation system 20′″ includes a separation container 40′″ that is positioned within an exterior container 310. The exterior container 310 can contain the separation container 40′″ similar to the outer wall 24 and the lid 26, discussed above. The exterior container 310, however, can include slots or connection regions 312 to engage pegs on a base, such as the base 22. The slots 312 can connect with the pegs in a bayonet manner for efficient and quick connection of the separation container 40′″ and the exterior container 310 with the base.

The system to withdraw the adipose particles 230 from the separation container 40, 40′, 40″, 40′″ can be performed for any appropriate reason. For example, the adipose tissue particles 230 can be re-introduced to the same patient from whom the whole adipose tissue sample 200 is withdrawn for a substantially autologous procedure. Alternatively, or in addition thereto, a portion of the adipose particles 230 can be supplied to an alternative or different patient. Various procedures can be performed with the adipose particles 230, such as selected cosmetic procedures requiring the introduction of adipose particles into a patient, such as for reconstructive surgery. Alternatively, or in addition thereto, the adipose particles 230 can be introduced into a patient for healing and other appropriate purposes.

Figure 8A:
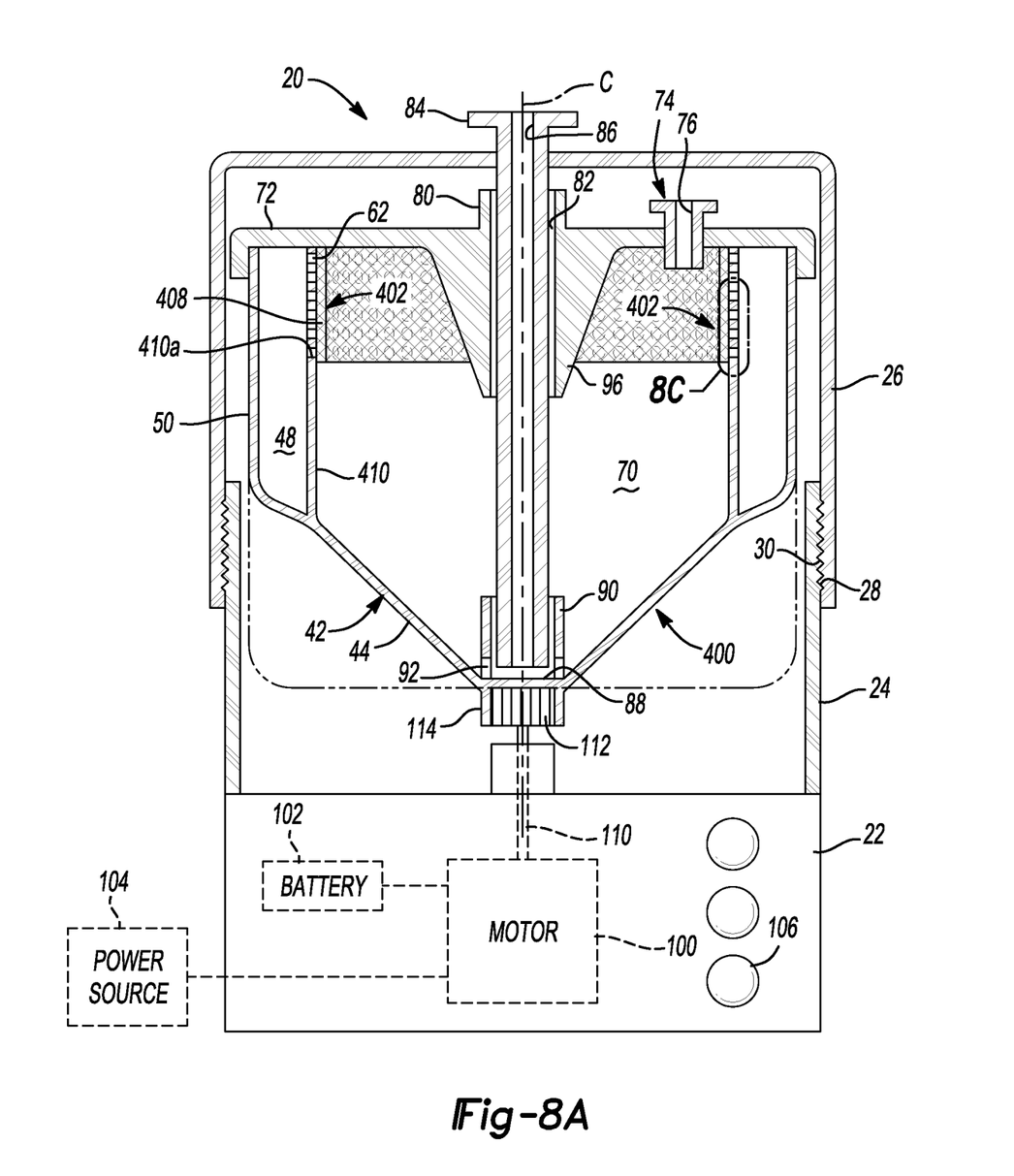
FIG. 8A illustrates a cross-section view of a separation container according to various embodiments.
Figure 8B:
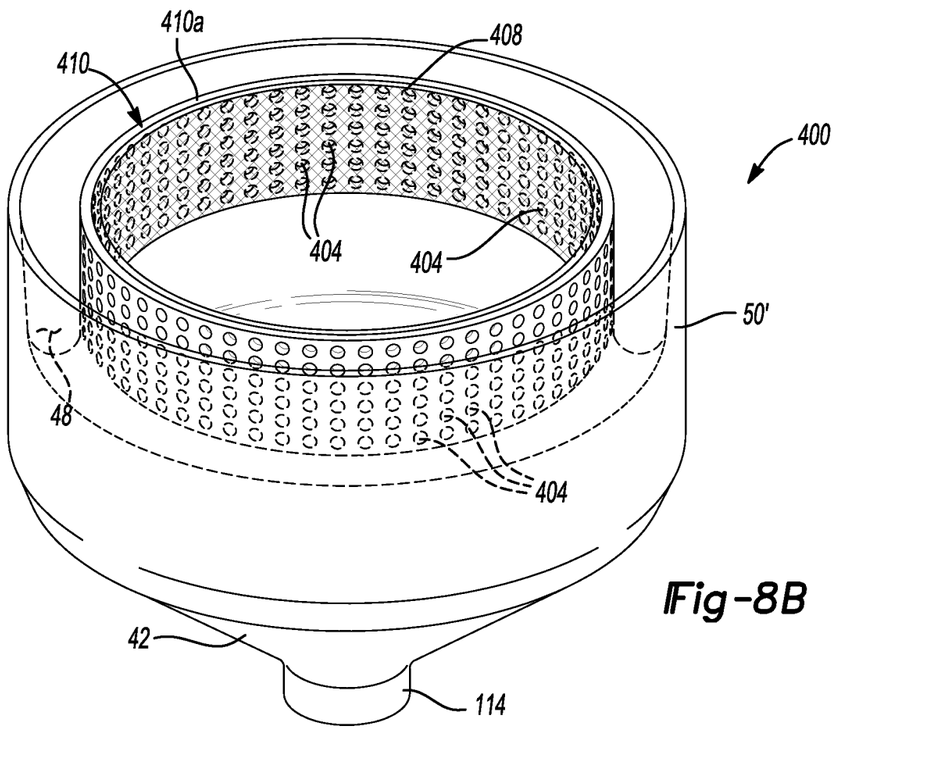
FIG. 8B illustrates a perspective view of a separation container according to various embodiments.
Figure 8C:
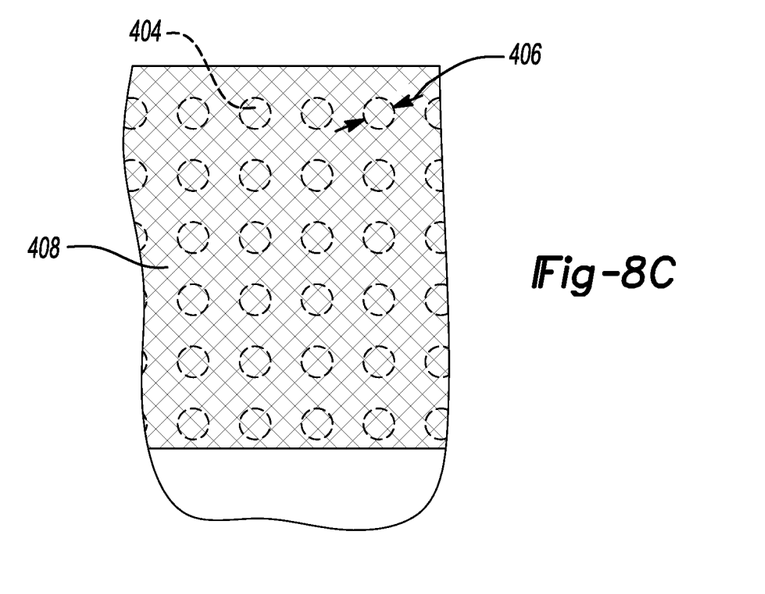
FIG. 8C illustrates a detail view of a portion of the separation container according to FIG. 8B.

According to various embodiments, the separation system 20 can include a separation container 400 as illustrated in FIGS. 8A-8C. The separation container 400 can include portions that are similar to the separation container 40 illustrated in FIG. 1, as discussed above. The portions of the separation system 20 that are substantially similar to the separation system discussed above will be referenced with the same reference numerals. Those similar portions, however, will not be discussed in detail here.

The separation container 400 can include a perforated wall portion 402 that includes one or a plurality of perforations or bores 404. The bores 404 can include a diameter or cross-section dimension 406 of any appropriate size. For example, the diameter 406 of the bores 404 can be dimensioned as discussed above, including about 0.05 inches. Further, the bores 404 can be provided at any appropriate density on an internal wall 410 of the separation container 400. The bores 404 can be separated from one another, such as at an on-center distance of about 0.05 inches to about 1 inch. In addition, a layer of porous material, such as felt or fabric, can be positioned near or adjacent to the bores 404.

The diameter or internal dimension 406 of the perforations 404 can be formed to provide or achieve a separation, as discussed above. For example, the separation container 400 can be used to remove a liquid phase or portion from a sample, such as a liquid from an adipose or fat sample. Accordingly, the dimension 406 of the bores 404 can be selected to ensure maintaining a selected fat or drier fat phase of the sample within the inner area 70 of the separation container 400.

As illustrated in FIGS. 8A and 8B, the separation container 400 can define the perforated area 402 along or at any appropriate portion of an internal wall 410. For example, the internal wall 410 can extend from a lower angle portion 44 of an external wall 42 to a top 410*a* of the internal wall 410. It will be understood, however, that the perforated area 402 can be formed substantially along the entire length of the internal wall 410.

The perforated wall portion 402 can be used similar to the perforated portion 60 discussed above. However, the perforated wall portion 402 can be provided with perforations of an appropriate size and density to eliminate or render unnecessary a filter portion within the annular collection basin 48. The liquid phase can be moved through the bores 404 into the basin 48 that exists between the internal wall 410 and the external basin wall 50. The perforated wall portion 402 can provide the sole physical portion to constrain the selected portion of the sample within the interior volume 70. For example, as illustrated above, a sample of material, such as whole adipose tissue, can be positioned in the interior separation region 70. The separation container 400 can then be spun around a central axis C to cause the whole sample to be moved against the internal wall 410 and the perforated wall portion 402. At a selected centrifugal force, such as about 100 times the force of gravity at sea level on Earth (gs) to about 2,000 gs, the liquid phase of the whole sample can be forced into the basin 48 and the perforated wall portion 402 can contain the selected portion of the whole adipose tissue sample within the separation basin 70. As an example, the separation can occur when the separation container 400 is spun at least about 2000 rpms for at least about 10 seconds, including at least about 30 seconds.

According to various embodiments including the separation container 400, the whole adipose tissue sample can be positioned within a separation region 70 and the separation container 400 can be spun at a selected rate. The basin 48 can collect or contain the liquid portion of the whole sample and can be positioned as illustrated in FIG. 8A. The basin 48 can also be provided to extend with any appropriate configuration or volume around the wall of the separation container 400. For example, as illustrated by the phantom wall 50′ in FIG. 8B, the exterior basin wall 50′ can extend to any appropriate region of the separation container 400. The position or extent of the exterior wall 50′ can be used to select a volume of the basin 48. The volume of the basin 48 can be augmented, for example by moving the position of the exterior wall 50′, to ensure an appropriate volume of the liquid is removed from the whole sample.

In addition to the bores 404, the material 408 can be provided or positioned interior or on an interior surface of the inner wall 410. The material 408 can include a material with bores or a porous material, such as a felt material including that discussed above. Exemplary felts can include the polyester felt including the 22 oz. felt sold by Superior Felt & Filtration, LLC. The material 408 can extend along the entire length or extent of the inner wall 410 or over only the perforated region or wall portion 402. The material 408 can be any appropriate material, such as a woven material or felt material that includes a selected porosity.

The material 408 can be held relative to the perforated portion 402 with appropriate mechanisms, such as adhering the material 408 near the perforated portion 402. The adhesive can include appropriate insoluble epoxies, such as two part epoxies, or other curable or non-cured adhesives.

The porosity of the material 408 can be selected to achieve a selected separation, such as a removal of a liquid phase from a whole sample. Also, the porosity of the material can have an average cross-sectional opening that can be different, such as smaller than that of the bores 404. For example the average cross-sectional area of the pores in the material 408 can be about 30% to about 70%, including about 50% smaller than the average cross-sectional area opening of the bores 404. The cross-sectional area of the bores 404 can be selected and designed to be based on the size of the cannula or instrument that is used to withdraw the whole sample. I can be selected to select the cross-sectional area bores 404 to be less than a diameter of the cannula for withdrawing the whole sample. This can allow the particles of the whole sample to generally be larger than the bores 404 during at least a portion of the separation. This can, further, hold the particles of the whole sample, such as adipose particles, within the separation region 70 and not allow them to travel into the basin 48, at least in any substantial or determinative amount.

The average cross-sectional opening can be determined or measured in any appropriate manner. For example, it can be an average of a cross-sectional area of the pores in the material 408 and/or an average of the cross-sectional area of the bores 404. Alternatively, or in addition thereto, it can be defined as the diameter of a member to pass through the material 408 or perforated portion 402.

The bores 404, when used in combination with material 408, can be any appropriate size to support the material 408 to allow for the passage of a liquid into the basin 48. For example, the bores 404 can include a cross-sectional dimension substantially enlarged to allow for quick passage of a liquid once it has moved through the material 408. The material 408 can include a porosity of a selected size to achieve the selected separation, such as substantially only a passage of a liquid or water phase into the basin 48 from the separation area 70, as discussed above. According to various embodiments, the material 408 can provide for the sole limiting or selection factor for separation of a selected portion of the material from the separation area 70 into the basin 48.

Regardless of the configuration of the separation containers, including those discussed above, a single container can be used to separate the liquid phase from a solid or particle phase of an adipose tissue sample according to the various embodiments. The whole adipose tissue sample can be introduced into the container 40, 40', 40", 40''', or 400 through the introduction port 74 and a rotation of the container can be used to separate the liquid phase from the adipose particle phase. The selected and dried or drier adipose particles can be removed from a central port. The drier adipose particles, therefore, can be prepared using a substantial single container and single step process.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A method of reducing fluid in a whole adipose tissue sample, comprising:
    obtaining a whole adipose tissue sample from a patient;
    placing the obtained whole adipose tissue sample into a first separation region of a separation container having a collection basin surrounding at least a portion of the first separation region, wherein the first separation region is centered on a central axis of the separation container;
    surrounding the separation container with an exterior container;
    spinning the first separation region within the exterior container about the central axis of the separation container to place a centrifugal force on the obtained whole adipose tissue sample placed in the separation container;
    forcing at least a portion of the whole adipose tissue sample radially outward from the central axis against an inner wall surface near a perforated wall portion, wherein the inner wall surface extends radially around the central axis;
    moving a volume of a liquid phase through the perforated wall portion of the separation container into the collection basin surrounding at least a portion of the first separation region while spinning the separation container;
    containing adipose particles of the whole adipose tissue sample within the first separation region;
    collecting adipose particles in a withdrawal area of the first separation region after the volume of the liquid phase has been removed; and
    withdrawing the adipose particles while maintaining the separation container within the exterior container.

2. The method of claim 1, further comprising:
    connecting the separation container to a motor; and
    operating the motor to spin the separation container;
    wherein the motor is operated to spin the separation container at least at about 2000 rotations per minute for at least about 30 seconds.

3. The method of claim 2, wherein operating the motor to spin the separation container induces the centrifugal force on the whole adipose tissue sample placed in the separation container;
    wherein moving a volume of the liquid phase includes forcing a liquid portion of the whole adipose tissue sample through the perforated wall portion having bores with a first passage cross-section appropriate to contain the adipose particles within the first separation region.

4. The method of claim 3, further comprising:
    placing a material defining a second passage cross-section over the perforated portion;
    wherein the second passage cross-section is less than the first passage cross-section.

5. The method of claim 4, further comprising:
    wherein the liquid phase is operable to move through at least the perforated portion, the material, and through a portion of the whole adipose tissue sample.

6. The method of claim 5, further comprising:
    maintaining the separation container substantially sterile while placing the obtained whole adipose tissue sample into the first separation region and withdrawing the drier adipose particles.

7. The method of claim 1, wherein moving the volume of the liquid phase through the perforated wall portion of the separation container into the collection basin includes moving at least one of about 30%, about 50%, about 70%, about 80%, or about 90% of the liquid phase from the whole adipose tissue sample.

8. The method of claim 1, wherein withdrawing the adipose particles includes accessing the separation container through an access port through the exterior container to allow extraction of a drier portion of the whole adipose sample from the separation container.

9. The method of claim 8, wherein withdrawing the adipose particles further includes withdrawing the drier portion of the whole adipose sample from the separation container through a tube extending from the access port.

10. The method of claim 1, further comprising:
moving the volume of the liquid phase through a porous material covering at least a first plurality of throughbores of a plurality of throughbores that are formed through the perforated wall portion of the separation container.

11. A method of reducing fluid in a whole adipose tissue sample, comprising:
placing a whole adipose tissue sample into a first separation region of a separation container having a collection basin surrounding at least a portion of the first separation region, wherein the first separation region is centered on a central axis of the separation container;
forming a drier volume of adipose tissue by rotating the first separation region about the central axis to move a volume of a liquid phase of the whole adipose tissue sample radially outward from the central axis through at least one bore of a perforated wall portion of the separation container into the collection basin surrounding at least a portion of the first separation region; and
withdrawing at least a portion of the drier volume of adipose tissue from the first separation region of the separation container.

12. The method of claim 11, wherein withdrawing at least the portion of the drier volume of adipose tissue from the first separation region of the separation container occurs while the separation container is maintained within an exterior container.

13. The method of claim 11, wherein forming the drier volume of adipose tissue further includes:
forcing at least a portion of the whole adipose tissue sample against an inner wa surface near the perforated wall portion defining the at least one bore.

14. The method of claim 13, wherein forcing at least the portion of the whole adipose tissue sample against an inner wall surface includes spinning the separation container around the central axis of the separation container to place a centrifugal force on the whole adipose tissue sample placed in the separation container.

15. The method of claim 14, further comprising:
ceasing spinning of the separation container; and
containing the drier volume of adipose tissue within the first separation region.

16. The method of claim 15, wherein containing the drier volume of adipose tissue within the first separation region includes collecting adipose particles in a withdrawal area of the first separation region after the volume of the liquid phase has been removed into the collection basin.

17. The method of claim 11, wherein forming the drier volume of adipose tissue further includes moving the volume of the liquid phase of the whole adipose tissue sample through a porous material covering the at least one bore.

18. The method of claim 11, further comprising:
maintaining the separation container within an exterior container during all of placing the whole adipose tissue sample into the first separation region of the separation container, forming the drier volume of adipose tissue, and withdrawing at least the portion of the drier volume of adipose tissue from the separation container.

19. A method of reducing fluid in a whole adipose tissue sample, comprising:
placing a whole adipose tissue sample into a first separation region of a separation container having a collection basin surrounding at least a portion of the first separation region;
operating a system to spin the separation container to form a drier volume of adipose tissue by moving a volume of a liquid phase of the whole adipose tissue sample through a porous material and at least one bore of a perforated wall portion of the separation container into the collection basin surrounding at least a portion of the first separation region, wherein the porous material is placed over the at least one bore; and
withdrawing at least a portion of the drier volume of adipose tissue from the first separation region of the separation container; wherein withdrawing at least the portion of the drier volume of adipose tissue includes withdrawing at least the portion of the drier volume through a port through an exterior container and a tube extending from the port to a collection region of the first separation region.

20. The method of claim 19, further comprising:
placing the separation container within the exterior container and placing the whole adipose tissue sample into the first separation region of the separation container.

21. The method of claim 20, further comprising:
maintaining the separation container within the exterior container during the withdrawing at least the portion of the drier volume of adipose tissue from the first separation region of the separation container.

22. The method of claim 19, wherein operating the system to spin the separation container includes operating the system to spin the separation container about a central axis of the separation container.

* * * * *

UNITED STATES PATENT AND TRADEMARK OFFICE
CERTIFICATE OF CORRECTION

PATENT NO. : 9,604,159 B2
APPLICATION NO. : 14/033944
DATED : March 28, 2017
INVENTOR(S) : Leach et al.

Page 1 of 1

It is certified that error appears in the above-identified patent and that said Letters Patent is hereby corrected as shown below:

In Column 13, Line 47, in Claim 13, delete "wa" and insert --wall-- therefor

Signed and Sealed this
First Day of May, 2018

Andrei Iancu
*Director of the United States Patent and Trademark Office*